(12) United States Patent
Leroux et al.

(10) Patent No.: US 11,408,819 B2
(45) Date of Patent: Aug. 9, 2022

(54) PROCESS AND SYSTEM FOR IDENTIFYING THE GRAM TYPE OF A BACTERIUM

(71) Applicant: BIOMÉRIEUX, Marcy l'Etoile (FR)

(72) Inventors: Denis Leroux, Trevoux (FR); Eric Laloum, Paris (FR); Pierre Mahe, Lans en Vercors (FR); Rony Midahuen, Fontaine (FR); Philippine Barlas, La Buisse (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 251 days.

(21) Appl. No.: 16/310,487

(22) PCT Filed: Jun. 13, 2017

(86) PCT No.: PCT/EP2017/064454
§ 371 (c)(1),
(2) Date: Dec. 17, 2018

(87) PCT Pub. No.: WO2017/216190
PCT Pub. Date: Dec. 21, 2017

(65) Prior Publication Data
US 2019/0323948 A1    Oct. 24, 2019

(30) Foreign Application Priority Data

Jun. 16, 2016 (EP) .................................... 16174717

(51) Int. Cl.
*G01N 21/25* (2006.01)
*C12Q 1/04* (2006.01)
*G01N 21/01* (2006.01)
*G01N 21/17* (2006.01)

(52) U.S. Cl.
CPC .............. *G01N 21/25* (2013.01); *C12Q 1/04* (2013.01); *G01N 21/01* (2013.01); *G01N 2021/174* (2013.01)

(58) Field of Classification Search
None
See application file for complete search history.

(56) References Cited

U.S. PATENT DOCUMENTS

| | | | |
|---|---|---|---|
| 6,640,130 B1 * | 10/2003 | Freeman .............. | A61B 5/0059 382/128 |
| 2010/0291669 A1 * | 11/2010 | Robinson ........... | G01N 35/0099 435/287.3 |
| 2011/0033847 A1 * | 2/2011 | Walsh ...................... | C12Q 1/04 435/6.16 |

FOREIGN PATENT DOCUMENTS

WO    2010/077304 A2    7/2010

OTHER PUBLICATIONS

Leroux et al., Hyperspectral imaging applied to microbial categorization in an automated microbiology workflow, Proc. SPIE 9537, Clinical and Biomedical Spectroscopy and Imaging IV, 953726, Jul. 15, 2015 (Year: 2015).*
Yoon et al., Hyperspectral Reflectance Imaging for Detecting a Foodborne Pathogen: Campylobacter, Transactions of the ASABE, vol. 52(2): 651-662, 2009 (Year: 2009).*
Huang et al., Recent Developments in Hyperspectral Imaging for Assessment of Food Quality and Safety, Sensors 2014, 14, 7248-7276 (Year: 2014).*
Rigaill et al., Evaluation of New bioMerieux Chromogenic CPS Media for Detection of Urinary Tract Pathogens, Journal of Clinical Microbiology, May 20, 2015 (Year: 2015).*
Jul. 14, 2017 International Search Report issued in International Patent Application No. PCT/EP2017/064454.
Jul. 14, 2017 Written Opinion issued in International Patent Application No. PCT/EP2017/064454.
Bosoon Park et al. "Hyperspectral Microscope Imaging Methods To Classify Gram-Positive and Gram-Negative Foodborne Pathogenic Bacteria". Transactions of the American Society of Agricultural and Biological Engineers, St. Joseph, MI, US, vol. 58, No. 1, Jan. 1, 2015, pp. 5-16.
Tatiana Luna-Pineda et al. "Spectroscopic Characterization of Biological Agents Using FTIR, Normal Raman and Surface-Enhanced Raman Scattering". Proceedings of the SPIE—The International Society for Optical Engineering, vol. 6654, Apr. 9, 2007-Apr. 27, 2007, pp. 1-11.
Mathilde Guillemot et al. "Hyperspectral Imaging for Presumptive Identification of Bacterial Colonies on Solid Chromogenic Culture Media". Optical Sensing II, SPIE, 1000 20th St., Bellingham, WA, 98225-6705, USA, vol. 9887, Apr. 27, 2016, pp. 98873L-1 thorugh 98873L-11.
Åsmund Rinnan et al. "Review of the Most Common Pre-Processing Techniques for Near-Infrared Spectra". Trends in Analytical Chemistry, vol. 28, No. 10, 2009, pp. 1201-1222.
Abraham Savitzky et al. "Smoothing and Differentiation of Data by Simplified Least Squares Procedures" . Analytical Chemistry, vol. 36, No. 8, Jul. 1964, pp. 1627-1639.
Éric Laloum. "Une Méthode Chimiométrique Originale D'Identification De Produits Par Spectroscopie Proche Infrarouge [An Original Chemometric Method for Identifying Products by Near Infrared Spectroscopy]". Spectra Analyse, vol. 33, No. 237, Apr.-May 2004, pp. 34-36.

* cited by examiner

*Primary Examiner* — Louise W Humphrey
*Assistant Examiner* — Srikanth Patury
(74) *Attorney, Agent, or Firm* — Oliff PLC

(57) ABSTRACT

A detection of the Gram type of a bacterial strain includes: illumination, in the wavelength range 415 nm-440 nm, of at least one bacterium of said strain having a natural electromagnetic response in said range; acquisition, in the range 415 nm-440 nm, of a light intensity reflected by, or transmitted through, said illuminated bacterium; and determination of the Gram type of the bacterial strain as a function of the light intensity acquired in the range 415 nm-440 nm.

6 Claims, 13 Drawing Sheets

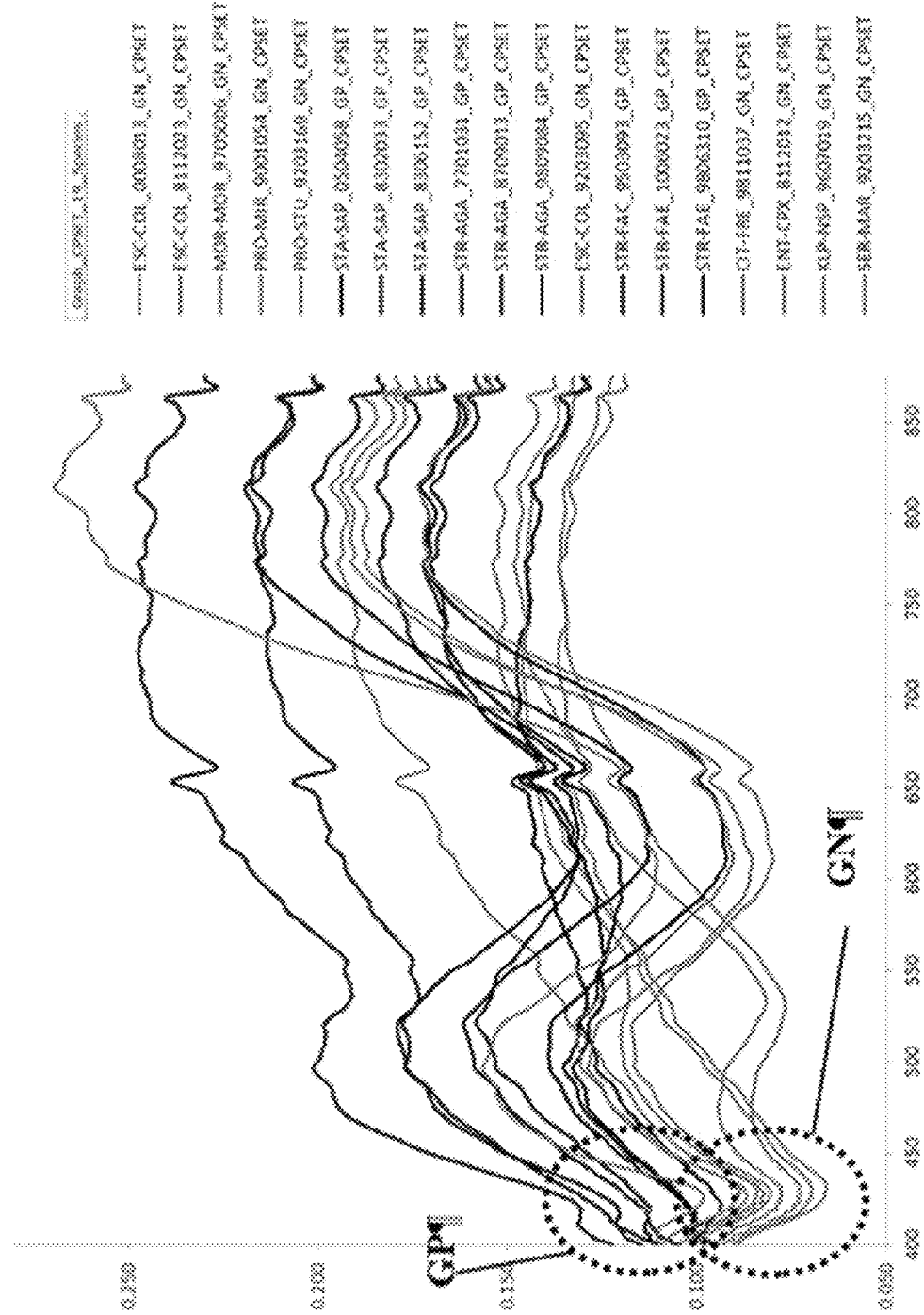
Figure 3A (CPSE)

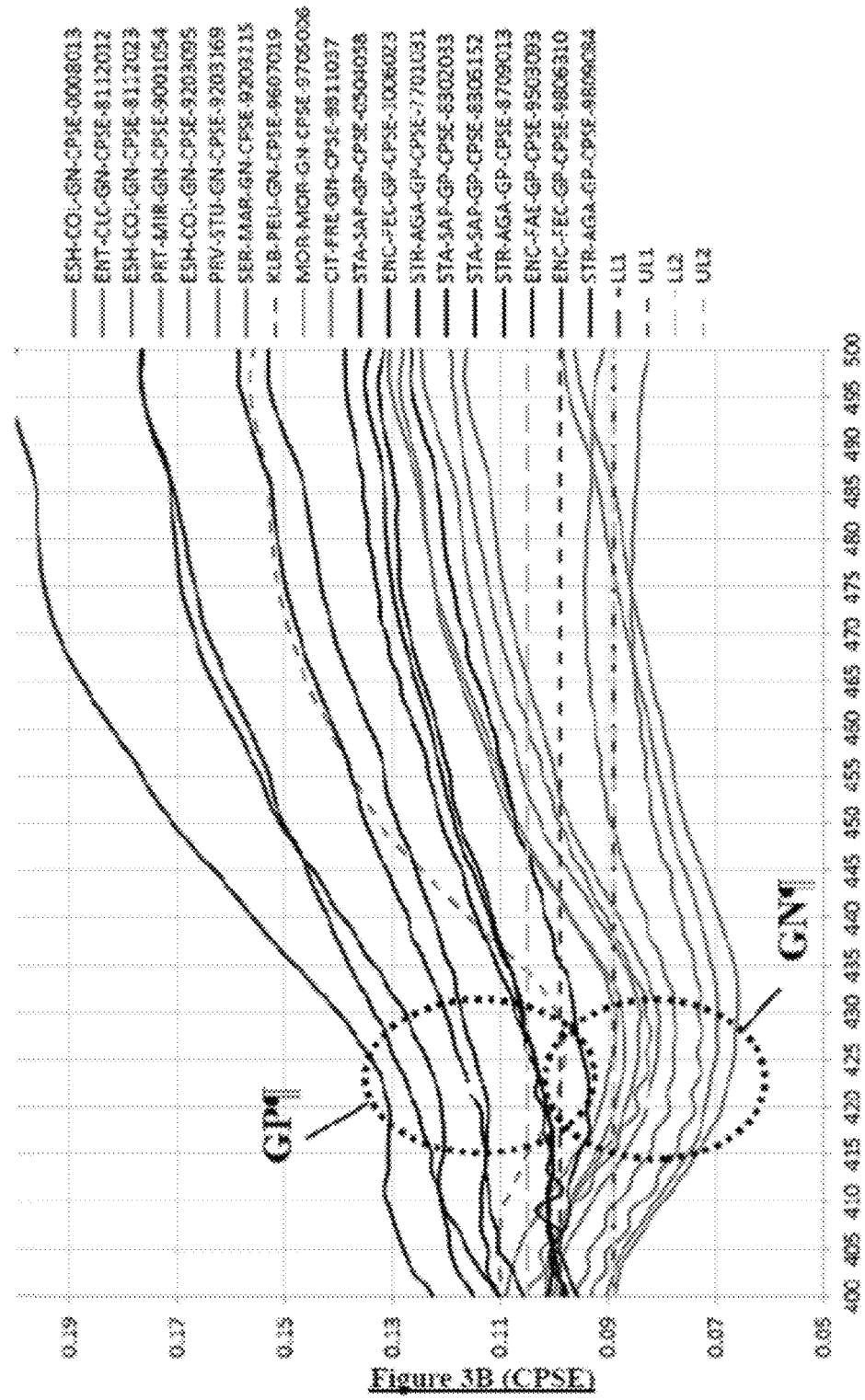

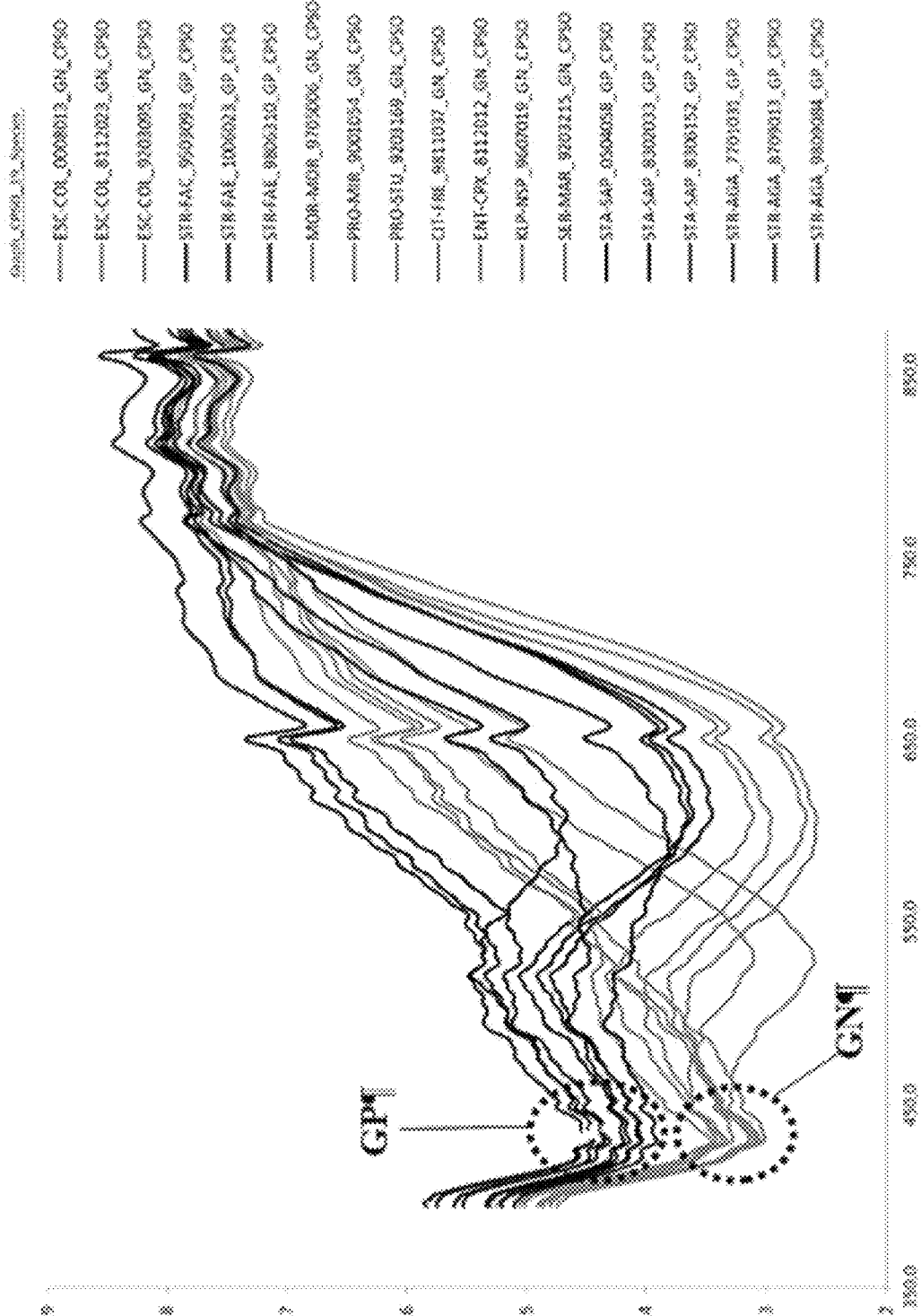
Figure 4A (CPSO)

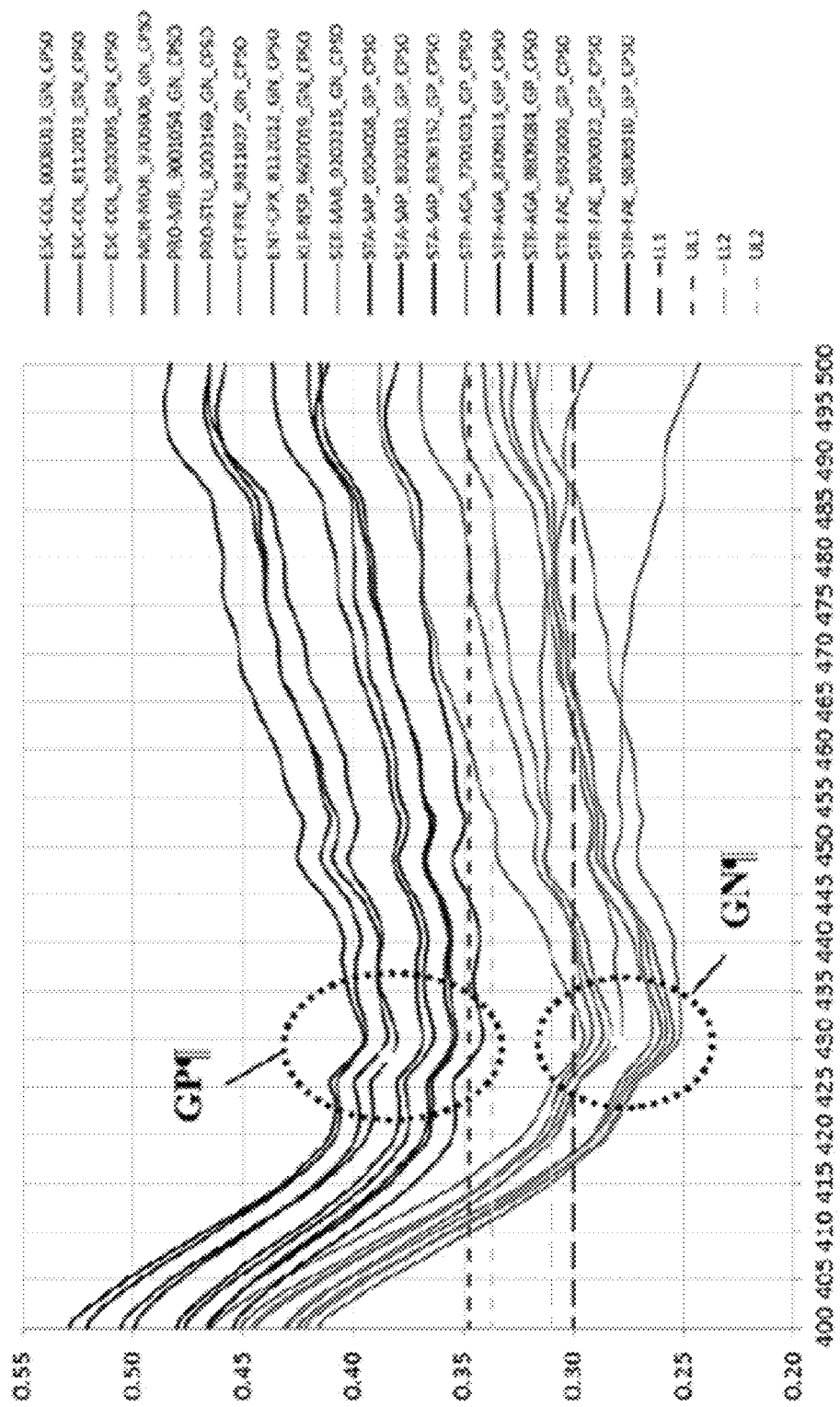
Figure 4B (CPSO)

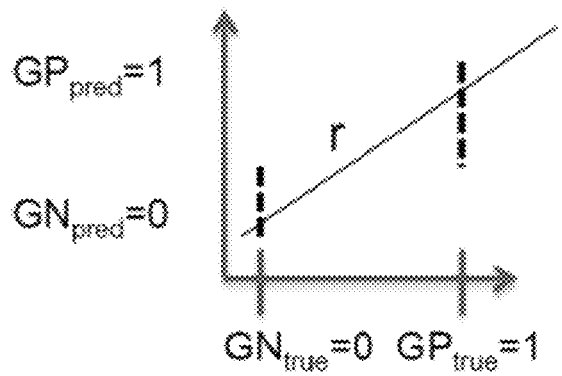

Figure 5

| Spectral preprocessing | Maximum value of the correlation | Wavelength $\lambda_c$ (nm) |
|---|---|---|
| Reflectance (raw) | 0.65 | 428 |
| Absorbance (Log 1/R) | -0.66 | 427.8 |
| Reflectance – 1$^{st}$ Der (SG) | 0.83 | 415.3 |
| Reflectance – 2$^{nd}$ Der (SG) | -0.79 | 434.1 |
| Absorbance – 1$^{st}$ Der (SG) | -0.84 | 417.4 |
| Absorbance – 2$^{nd}$ Der (SG) | 0.86 | 434.1 |
| SNV reflectance | -0.58 | 396.5 |
| Area normalized reflectance | 0.76 | 432 |
| Unit vector normalized reflectance | 0.77 | 432 |
| Area normalized absorbance | -0.6 | 432 |
| Unit vector normalized absorbance | -0.59 | 432 |
| Reflectance – 1$^{st}$ Der – unit vector normalized | 0.8 | 421.5 |
| Reflectance – unit vector normalized – 1$^{st}$ Der | 0.83 | 421.5 |
| Reflectance – 1$^{st}$ Der – SNV | 0.8 | 421.5 |

Figure 8

PROCESS AND SYSTEM FOR IDENTIFYING THE GRAM TYPE OF A BACTERIUM

FIELD OF THE INVENTION

The invention relates to the field of microbiological analysis, and in particular of the identification of the Gram type of a bacterium.

Advantageously, the invention applies to the analysis of a hyperspectral or multispectral image of a bacterial colony having grown in a non-chromogenic, non-fluorogenic and dye-free nutritive medium.

PRIOR ART

The Gram classification of a bacterial strain makes it possible to characterize the wall thereof, for example its peptidoglycan percentage, and is used in the taxonomy of bacteria or for evaluating their sensitivity to antibiotics. Two types of bacterium are thus distinguished, namely the Gram-"positive" bacteria and the Gram-"negative" bacteria. The knowledge of the Gram type of a bacterial strain makes it possible for example to select suitable tests for identifying the strain or carrying out antibiotic sensitivity testing, e.g. the choice of a suitable card for an antibiotic sensitivity test carried out by the Vitek© 2 automated device sold by the applicant.

Historically, the Gram type of a bacterial strain was determined by a manual technique known as "Gram staining", which comprises a large number of manual steps (fixing, staining, etching, washing, counterstaining, etc.) and therefore takes a long time to implement. Various techniques have therefore been developed for automating the detection of the Gram type of bacteria, in particular in order to process a large number of samples. However, these techniques mostly continue to modify the electromagnetic response of the bacteria or of their medium in order to make their Gram easily observable.

For example, a first type of technique consists in automating the staining of the bacterial membrane on microscope coverslips, but the final step of deciding on the Gram type is still carried out by a technician who looks at the coverslips under a microscope. This type of technique is not therefore entirely automated, and is, moreover, difficult to automate. This is because the difference in colors between Gram-positive bacteria and Gram-negative bacteria may be subtle, explaining why the involvement of a laboratory technician is still required.

A second type of technique consists in placing bacteria in the presence of a substrate which degrades by means of an enzymatic reaction initiated by the peptidoglycans of the bacterial membranes. This reaction produces chromophores or fluorophores, the concentration of which is an indication of the Gram. The term chromogenic or fluorogenic "staining" of bacteria is normally used. While prior art techniques of this type can be automated, for example by measuring the light intensity of the chromophores/fluorophores using a suitable device (e.g. spectrometer/fluorometer) and then by comparing, using a computer program, the intensity measured with predefined threshold values, they nevertheless entail the design of particular chromophore or fluorogenic substrates, which are often expensive.

In addition, regardless of the technique used, the bacteria undergo a modification of their natural state (e.g. they comprise dyes, they have bound chromogenic or fluorescent labels, etc.), and cannot therefore be used for subsequent characterization tests (e.g. determining antibiotic sensitivity).

SUMMARY OF THE INVENTION

The objective of the present invention is to provide a process for determining the Gram type of a strain of bacterium which is automatic and which does not require labeling or staining of the bacterium in order to determine its Gram.

To this effect, a subject of the invention is a process for detecting the Gram type of a bacterial strain, comprising:
  illumination, in the wavelength range 415 nm-440 nm, of at least one bacterium of said strain having a natural electromagnetic response in said range;
  acquisition, in the range 415 nm-440 nm, of a light intensity reflected by, or transmitted through, said illuminated bacterium; and
  determination of the Gram type of the bacterial strain as a function of the light intensity acquired in the range 415 nm-440 nm.

For the purposes of the invention, the expression "natural electromagnetic" response is intended to mean that the bacterium is not modified by means of elements (dye, chromogene, fluorogene, etc.) which modify its electromagnetic response to an illumination at least in the wavelength range of interest. For example, a colony of the strain is cultured in a non-colored, non-chromogenic and non-fluorescent nutritive medium and the illumination/acquisition is carried out directly on the colony still present in its medium.

In other words, the inventors have discovered a wavelength range in which a bacterium "naturally" has an electromagnetic signature characteristic of its Gram type. The process according to the invention thus consists in measuring this signature and then in extracting the Gram type therefrom. Thus, it is not necessary to use a chromogenic or fluorogenic substrate or dyes. Moreover, the process according to the invention is fast insofar as it consists in illuminating, measuring a spectrum and carrying out processing, in particular computer processing, of this spectrum.

According to one embodiment, said bacterium also has a natural electromagnetic response in the wavelength range 750 nm-800 nm; and:
  the illumination of said bacterium is also carried out in the wavelength range 750 nm-800 nm;
  the acquisition of a light intensity reflected by, or transmitted through, the illuminated bacterium is also carried out in the range 750 nm-800 nm; and
  the determination of the Gram type of the bacterial strain is carried out as a function of the light intensities acquired in said ranges 415 nm-440 nm and 750 nm-800 nm.

In other words, the bacterium also comprises a natural electromagnetic signature in the range 750 nm-800 nm characteristic of its Gram. The detection of its Gram can also be carried out in this range. Advantageously, by combining the two wavelength ranges, a better accuracy is obtained in the determination of the Gram type.

According to one embodiment, the determination of the Gram type comprises:
  calculation of a reflectance or absorption factor of said illuminated bacterium as a function of the light intensity acquired;
  determination of the Gram type as a function of the reflectance or absorption factor calculated.

In other words, the reflectance or absorption factor reflects more faithfully the natural electromagnetic behavior of the bacterium, since this corrects the measured signal with respect to the spectral behavior of the illumination and the sensor (e.g. the white point, the black point, the non-uniformity of the spectrum of the illumination in the range(s) of interest, etc.) and thus allows a more accurate detection.

In particular, the determination of the Gram type comprises:
calculation of a first derivative in the wavelength of the reflectance or absorption factor calculated;
determination of the Gram type as a function of the first derivative calculated.

In other words, the inventors have noted that the electromagnetic signature characteristic of the Gram is more discriminating when deriving the light intensity or the reflectance/absorption factor, which allows a more accurate detection.

According to one embodiment, the determination of the Gram type is carried out as a function of the light intensity at a single wavelength of the range 415 nm-440 nm, in particular the wavelength 420 nm. More particularly, the determination of the Gram type comprises:
comparison of a value equal to the light intensity at 420 nm, or calculated therefrom, to a predetermined first threshold and a predetermined second threshold separating the Gram-positive straining from the Gram-negative staining, the first threshold being greater than the second threshold;
determination of negative Gram if said value is above the first threshold and determination of positive Gram if said value is below the second threshold.

In other words, a good level of accuracy in the detection is obtained even with a single wavelength, in particular at 420 nm. In particular, a simple thresholding makes it possible to have a minimum accuracy of 80%. This makes it possible to simplify the computer calculations and/or the illumination and the sensor. The determination can be carried out on the basis of the light intensity itself or after a preprocessing thereof (e.g. filtering of the noise, removal of an offset, passage to a first or second derivative, etc.).

According to one embodiment, the determination of the Gram type comprises the application of a predetermined linear prediction linking the light intensity acquired, or a value calculated therefrom, to the Gram type, followed by thresholding of the result of the linear prediction applied.

As a variant, the determination of the Gram type comprises the application of a two-class classification of SVM type to the light intensity acquired, or to a value calculated therefrom.

According to one embodiment, the illumination and the acquisition are carried out directly on a sample comprising a colony of the bacterial strain and a nutritive medium in which said colony has grown.

In other words, the invention advantageously directly applies to a sample usually produced in the microbial work flow, namely colony growth, for example on Petri dishes, such that the invention does not involve the provision of a specific sample preparation in order to be carried out. Moreover, a colony comprises a very large amount of bacteria of the strain. Thus, measuring the intensity reflected by, or transmitted through, a colony makes it possible to naturally increase the degree of reliability of the detection, the intensity being naturally averaged for example. However, it will be noted that the invention applies to the individual detection of a bacterium, it being possible for a statistical study to be carried out when several bacteria are observed. Likewise, the invention obviously applies to media other than those normally used in Petri dishes (usually agars), for instance liquid media in which the bacteria are in suspension.

In particular, the determination of the Gram type is carried out as a function of said nutritive medium. In other words, the nutritive medium also has its own "electromagnetic signature" in the wavelength ranges of interest, and can therefore disrupt the detection of the Gram type. By taking the nutritive medium into account, either during the processing, or during the choice of the medium used for the growth of the colony, a better detection accuracy is obtained.

In particular, an opaque substrate at the surface of which a colony has grown, said substrate preferably having a reflectance p of less than or equal to 10%, preferably less than or equal to 5%. In particular, in the context of a detection based on the reflected light intensity, a better accuracy is obtained.

According to one embodiment, the acquisition of the light intensity comprises the acquisition of a hyperspectral or multispectral image of a colony of bacteria of the strain, and the light intensity is determined as a function of at least one pixel of said image corresponding to the colony. In particular, the light intensity is equal to the mean pixels of said image corresponding to the colony.

In other words, the hyperspectral or multispectral imaging makes it possible to simultaneously acquire the two ranges 415 nm-440 nm and 750 nm-800 nm by means of a single sensor, and also makes it possible to obtain a spatial mean of each wavelength acquired over several pixels, thereby increasing the accuracy of the detection. As is known per se, the term "hyperspectral" corresponds to the acquisition of a wavelength range as a whole (to within a sampling spacing), whereas the term "multispectral" generally refers to the acquisition in distinct ranges.

A subject of the invention is also a system for carrying out the process which has just been described. In particular, a subject of the invention is a system for detecting the Gram type of a bacterial strain, comprising:
an illumination configured to illuminate, in the wavelength range 415 nm-440 nm, at least one bacterium of the strain;
a sensor configured to acquire, in the range 415 nm-440 nm, a light intensity reflected by, or transmitted through, said illuminated bacterium; and
a computer unit configured to determine the Gram type of the bacterial strain as a function of the light intensity acquired in the range 415 nm-440 nm.
According to one embodiment:
the illumination is configured to illuminate said bacterium in the wavelength range 750 nm-800 nm;
the sensor is configured to acquire, in the wavelength range 750 nm-800 nm, a light intensity reflected by, or transmitted through, said illuminated bacterium; and
the computer unit is configured to determine the Gram type of the bacterial strain as a function of the light intensity acquired in said ranges 415 nm-440 nm and 750 nm-800 nm.

According to one embodiment, the system is configured to illuminate, and to acquire the image of, a sample comprising a colony of bacteria of said strain and a nutritive medium in which said colony has grown, in particular a Petri dish.

BRIEF DESCRIPTION OF THE FIGURES

The invention will be understood more clearly from reading the description which follows, given only by way of example, and provided in relation to the appended drawings, in which identical references denote identical or analogous elements, and in which

FIGS. 3A and 3B are plots illustrating spectra of reflectance of bacterial colonies having grown on a transparent medium;

FIGS. 4A and 4B are plots illustrating spectra of reflectance of bacterial colonies having grown on an opaque medium;

FIG. 5 is a plot illustrating the linear prediction model used for the prediction according to one variant of the invention;

FIG. 8 illustrates a table of different variables of decisions that can be used for the prediction according to the invention;

DETAILED DESCRIPTION OF THE INVENTION

In the subsequent text, the notation $A_{i,j}$ relates to the element of the $i^{th}$ row and of the $j^{th}$ column of the matrix A.

Figure 1:
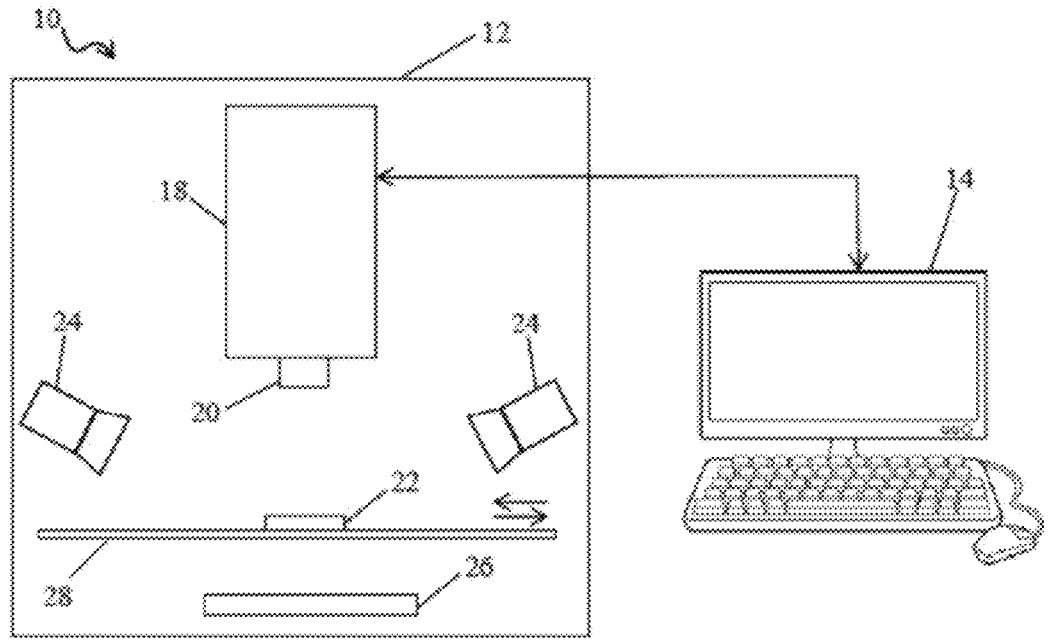
FIG. 1 is a diagrammatic view of a system for predicting the Gram type according to the invention.

Referring to FIG. 1, a system 10 for detecting the Gram type of a bacterial strain according to a first embodiment comprises:
- a device 12 for acquisition of a hyperspectral image; and
- a data-processing computer unit 14 connected (e.g. by a wired or wireless link) to the device 12 for controlling it and for receiving and processing the images acquired by the device 12.

The device 12, for example a hyperspectral imaging system of reference "Pika II" from the company Resonon, Mont. USA, comprises:
- a "hyperspectral" camera 18, consisting of a digital sensor comprising a network of elementary sensors, for example a digital sensor of CCD or CMOS type, sensitive in the wavelength range $[\lambda_{min}; \lambda_{max}]=[400; 900]$ nanometers, and of a light-scattering element or of a spectrograph for selecting a wavelength to be acquired by the sensor;
- an objective 20 for focusing, on the digital sensor of the camera 18, the optical image of a Petri dish 22, of which it is desired to acquire a hyperspectral image;
- a front illumination 24, for example consisting of one or more allogenic lamps, e.g. 2 or 4 lamps, capable of emitting light in the range $[\lambda_{min}; \lambda_{max}]$, for producing a uniform front illumination of the Petri dish 22. For example, the illuminations are white-light lamps;
- a back illumination 26, for example consisting of a white-light LED matrix, for producing a uniform back illumination of the Petri dish 22 in the range $[\lambda_{min}; \lambda_{max}]$; and
- a carriage 28 on which the Petri dish 22 sits and which allows the latter to pass in front of the objective 20 in order to obtain a whole image of the dish 22 by scanning.

The device 12 is for example configured to acquire the image of a region of 90 millimeters by 90 millimeters with a sampling spacing of 160 micrometers (spatial resolution estimated at 300 micrometers) and with a spectral resolution of 1.7 nanometers over the range $[\lambda_{min}; \lambda_{max}]$.

The device 12 thus produces a digital image HSI of the light reflected by the Petri dish, having N rows and M columns, the Petri dish 22 preferably being open (i.e. without its lid):

$$HSI(\lambda) = \begin{pmatrix} Rad_{1,1}(\lambda) & \cdots & Rad_{1,j}(\lambda) & \cdots & Rad_{1,M}(\lambda) \\ \vdots & \ddots & \vdots & \vdots & \vdots \\ Rad_{i,1}(\lambda) & \cdots & Rad_{i,j}(\lambda) & \cdots & Rad_{i,M}(\lambda) \\ \vdots & \vdots & \vdots & \ddots & \vdots \\ Rad_{N,1}(\lambda) & \cdots & Rad_{N,j}(\lambda) & \cdots & Rad_{N,M}(\lambda) \end{pmatrix} \quad (1)$$

The radiance of a pixel, commonly referred to as "light intensity", corresponds here to the amount of light incident on the surface of the corresponding elementary sensitive site of the sensor of the camera 18 during the exposure period, as is known per se from the digital photography field for example.

Each pixel $Rad_{i,j}(\lambda)$ is composed of a digital spectrum of the radiance of the dish 22 corresponding to the pixel at various wavelengths $[\lambda_{min}; \lambda_{max}]$, the digital spectrum being expressed according to the relationship:

$$\forall (i, j) \in [1, N] \times [1, M]: Rad_{i,j}(\lambda) = \begin{pmatrix} Rad_{i,j}(\lambda_{min}) \\ Rad_{i,j}(\lambda_{min} + \Delta\lambda) \\ Rad_{i,j}(\lambda_{min} + 2 \times \Delta\lambda) \\ \vdots \\ Rad_{i,j}(\lambda_{min} + p \times \Delta\lambda) \\ \vdots \\ Rad_{i,j}(\lambda_{max}) \end{pmatrix} \quad (2)$$

wherein $\Delta\lambda$ is the spectral resolution and p is a positive integer belonging to $$\left[0, P = \frac{\lambda_{max} - \lambda_{min}}{\Delta\lambda}\right].$$

The acquisition wavelengths $\lambda_{min} p \times \Delta\lambda$ are usually denoted by the term "channels".

The data-processing unit 14 is for example a personal computer, a tablet, a smartphone, a server, a supercomputer, or more generally any system based on one or more microprocessor(s), in particular of DSP (digital signal processor)

type, based on circuits of FPGA type, based on circuits mixing these technology types, etc., configured to perform processing of the HSI images produced by the acquisition device 12. The unit 14 has in particular all the memories (RAM, ROM, cache memory, main memory, etc.) for storing the images produced by the device 12, computing instructions for implementing the process according to the invention, parameters used for this implementation and for storing the results of the intermediate and final calculations, in particular the Gram type determined. The unit 14 optionally comprises a display screen for visualizing the final result of the determination of the Gram type. Although a single processing unit is described, the invention obviously applies to processing carried out by several processing units (e.g. a unit fitted within the camera 18 for carrying out preprocessing of HSI images and a unit external to the device 12 for carrying out the rest of the processing). Moreover, the system can be supplemented with an interface which makes it possible to enter, into the unit 14, data relating to the sample, in particular the type of culture medium used when the prediction depends on the medium, for example by means of a keyboard/mouse and of a scroll-down menu available to the operator, a barcode/QR code reader which reads a barcode/QR code present on the Petri dish and comprising information on the medium, etc.

Figure 2:
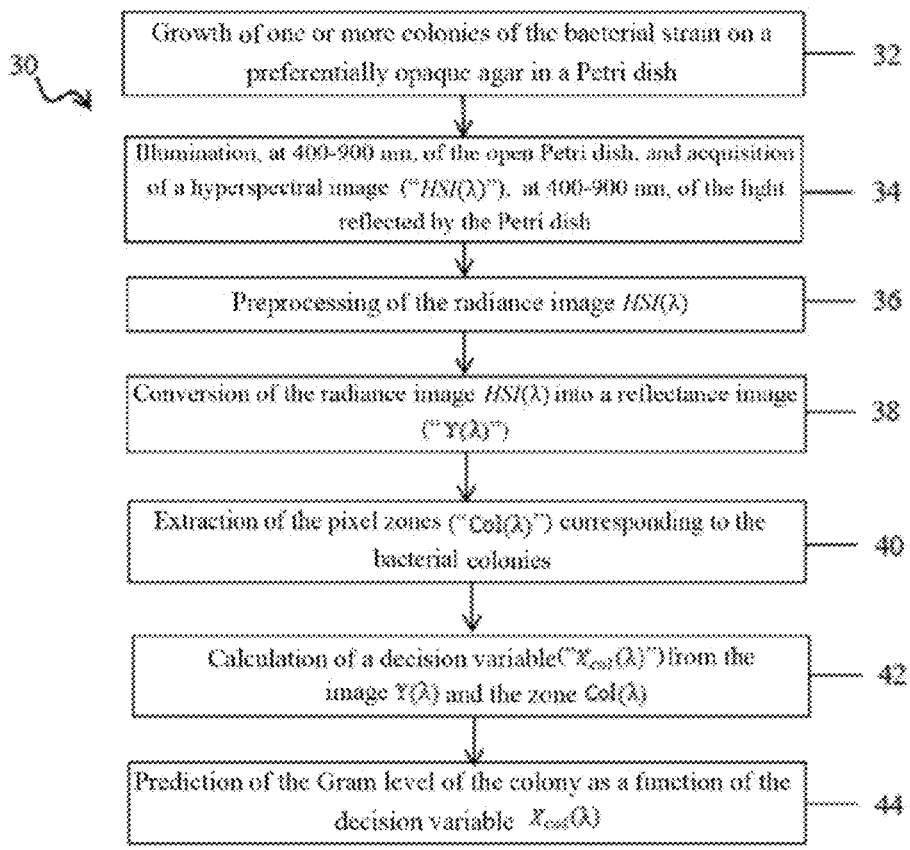
FIG. 2 is a flowchart of a process for predicting the Gram type carried out by means of the system of FIG. 1.

A process 30 for determining the Gram type of a bacterial strain by means of the system which has just been described is now detailed in relation to the flowchart of FIG. 2.

In a first step 32 of the process, at least one colony of the bacterial strain is cultured at the surface of a nutritive medium, or "culture" medium, deposited in a Petri dish. The main objective of the nutritive medium is to cause said colony to grow, and optionally to reinforce the accuracy of the detection of the Gram type by limiting the light disruptions. Preferably with regard to a detection of the Gram type as a function of the reflected light intensity, the nutritive medium is opaque, thereby increasing the degree of accuracy of the detection. In particular, the opaque medium has a reflectance factor $\rho$ of less than or equal to 10%, and preferably less than or equal to 5%, and even more preferentially less than or equal to 1%. For example, the culture medium is a "CPSO" agar ("CPS" agar comprising $SiO_2$ in order to opacify the medium), a "Columbia" agar (or "CNA" agar), a Columbia agar with 5% sheep blood (or "COS" agar), a Man, Rogosa, Sharpe agar ("MRSM" agar), a chocolate agar ("PVX" agar), etc.

Since this type of colony growth is conventional, it will not be subsequently described in greater detail. It can advantageously be performed manually by an operator, or automatically by means of an automated device for seeding in a manner known per se. Advantageously, the preparation is performed in such a way that the colonies, on the basis of which the prediction of the Gram type is carried out, are at a distance from one another and in such a way that the surface of a colony corresponds to a plurality of pixels in the image acquired by the device 12. This makes it possible in particular to facilitate their subsequent identification in the acquired image.

Once the growth of the colonies has ended, the Petri dish is opened, placed on the carriage 28, the illuminations 24 and 26 are turned on and at least one hyperspectral image HSI of the Petri dish is acquired, at 34, by means of the acquisition device 12 and stored in the processing unit 14, which carries out computer processing to determine the Gram type of the strain on the basis of the acquired images.

The unit 14 optionally begins, at 36, by preprocessing of the noise, consisting of one of the following processing operations or any combination of these processing operations:

a. correction of the noise of the sensor of the camera 18, in particular its offset, its spatial noise, etc., in a manner known per se;

b. processing of the parasitic, in particular specular, reflections forming "overly bright spots" in the HIS image, for example, thresholding performed in order to eliminate the pixels having values above a predetermined threshold, e.g. greater than or equal to two thirds of the maximum value that the pixels can have (i.e. greater than or equal to 170 in the case of pixels coded on 8 bits between 0 and 255);

c. radiometric processing making it possible to reduce the variations in the images caused by outside fluctuations such as variations in illumination, by dividing the HSI image by a reflected light intensity at a wavelength which does not vary with the type of bacterium and the type of agar used;

d. if several HSI images have been acquired, searching for and eliminating aberrant pixel values and/or averaging the acquired images.

The processing continues, at 38, with the conversion of the preprocessed HSI image, which stores radiance values at different wavelengths, into a hyperspectral image of reflectance in order to extract the signal generated by the Petri dish alone. This makes it possible in particular to filter the fluctuations in the emission spectrum of the illumination sources 24, 26. For example, a correction of the "flat field correction" (FFC) type is carried out in order to obtain the reflectance, this also having the advantage of correcting the pixel-to-pixel sensor response dispersions (dispersion of the dark current, dispersion of the gain, etc.). This conversion is for example a correction according to the relationships:

$$\forall (i, j) \in [1, N] \times [1, M], \forall p \in [0, P]:$$

$$\Upsilon_{i,j}(\lambda_{min} + p \times \Delta\lambda) = \frac{Rad_{i,j}(\lambda_{min} + p \times \Delta\lambda) - B_{i,j}(\lambda_{min} + p \times \Delta\lambda)}{W_{i,j}(\lambda_{min} + p \times \Delta\lambda) - B_{i,j}(\lambda_{min} + p \times \Delta\lambda)} \times m(\lambda_{min} + p \times \Delta\lambda) \quad (3)$$

wherein $\gamma(\lambda)$ is a reflectance image, W is a hyperspectral image, stored in the unit 14, of a neutral object of high reflectance and illuminated by the illuminations 24, 26, for example a sheet of uniform reflectance greater than 90% (e.g. a "white" sheet or one with a chart of gray less than 10%), and B is a hyperspectral image, stored in the unit 14, of a neutral object of low reflectance, for example the image of a black cover blocking the objective 20 and $m(\lambda_{min}+p\times\Delta\lambda)=1$ or equal to the mean of the matrix $W(\lambda_{min}+p\times\Delta\lambda)-B(\lambda_{min}+p\times\Delta\lambda)$.

The unit 14 implements, at 40, following step 38 or in parallel to the preceding steps, an algorithm for identifying the colonies of bacteria, e.g. from the $HSI(\lambda)$ or $\gamma(\lambda)$ image. Any conventional shape and object recognition algorithm can be used to extract a zone of the image, called "$Col(\lambda)$", corresponding to a colony. As a variant, this selection is carried out manually by an operator who selects this zone with the assistance of the display screen and of a pointing mechanism of the mouse type for example. By way of example, the zone $Col(\lambda)$ consists of a list of the pixel coordinates belonging to the colony. The pixel zones selected are stored by the unit 14.

The process continues, at 42, with the calculation of a decision variable $X_{col}(\lambda)$ as a function of the pixels of the image $\gamma(\lambda)$ included in the zone $Col(\lambda)$, this variable being that to which rules for prediction of the Gram type apply. In one variant, the decision variable $X_{col}(\lambda)$ is based solely on the image $\gamma(\lambda)$. In other variants, the image $\gamma(\lambda)$ is supplemented with or replaced by one or more other types of parameters calculated as a function of the reflectance image $\gamma(\lambda)$, as will be subsequently described in greater detail. To this effect, processing of the reflectance image $\gamma(\lambda)$ is thus optionally carried out. In particular, the unit 14 calculates one and/or the other of the following parameters:

i. an absorbance image $A(\lambda)$, for example by means of the Beer-Lambert transform (relationship (4)) or of the Kubelka-Munk transform (relationship (5)). Without being bound by theory, the inventors are of the opinion that Gram-negative bacteria differ from Gram-positive bacteria by a higher content of cytochromes which are absorbent in the range [415-440] nm, which makes it possible to characterize the conversion into absorbance image:

$$\forall (i,j) \in [1, N] \times [1, M], \forall p \in [0, P]:$$

$$A_{i,j}(\lambda_{min} + p \times \Delta\lambda) = \log\left(\frac{1}{Y_{i,j}(\lambda_{min} + p \times \Delta\lambda)}\right) \quad (4)$$

$$A_{i,j}(\lambda_{min} + p \times \Delta\lambda) = \frac{(1 - A_{i,j}(\lambda_{min} + p \times \Delta\lambda))^2}{2 \times A_{i,j}(\lambda_{min} + p \times \Delta\lambda)} \quad (5)$$

ii. a reflectance image $\gamma(\lambda)$ which has been normalized or an absorbance image $A(\lambda)$ which has been normalized in order to reduce the variabilities due to optical effects. The unit carries out for example an area normalization, a unit vector normalization, a mean normalization, a maximum normalization, a range normalization or a peak normalization. These normalizations are described for example in the document by K. Varmuza and P. Filzmoser, "*Introduction to Multivariate Statistical Analysis in Chemometrics*", CRC Press, 2009 and the document by A. Rinnan, F. van den Berg and S. Engelsen, "*Review of the most common pre-processing techniques for near-infrared spectra*", Trends in Analytical Chemistry, vol. 28, No. 10, 2009;

iii. the first derivative $$\frac{\partial}{\partial \lambda}$$

or second derivative $$\frac{\partial^2}{\partial \lambda^2}$$

of the wavelength of the reflectance image $\gamma(\lambda)$, which is normalized or non-normalized, or of the absorbance image $A(\lambda)$, which is normalized or non-normalized, in order to accentuate the changes in behavior of the spectrum and to reduce the baselines. Preferably, a polynomial local filtering algorithm is used to reduce the error propagation, advantageously an algorithm as described in the document by A. Savitzky and M. J. E. Golay "*Smoothing and differentiation of data by simplified least squares procedures*", Anal. Chem., vol. 36, pp. 1627-1639, 1964.

The Gram type of each colony is then predicted at 44 by the unit 14 as a function of the variable $X_{col}(\lambda)$ by applying predefined decision rules, variants of which are described below. The predicted Gram type is stored in the unit 44 and/or displayed on a screen. This prediction is for example delivered to another microbial analysis instrument for a subsequent step of identifying/characterizing the colony.

A. Single-Channel Approach

In a first variant, a single-variable and single-channel approach is implemented by the unit 14. According to this approach, the decision variable $X_{col}(\lambda)$ comes down to a single value taken at a predefined wavelength $\lambda_c$ in the wavelength range 415 nm-440 nm, e.g. the (normalized or non-normalized) reflectance of the colony, or the (normalized or non-normalized) absorbance of the colony, or the first derivative or the second derivative thereof.

In a first variant based on the reflectance, the unit 14 calculates, at 42, a spectrum of reflectance of the colony, e.g. a mean spectrum on the pixels of the colony according to the relationship:

$$\forall p \in [0, P]:$$

$$Y_{col}(\lambda_{min} + p \times \Delta\lambda) = \frac{1}{N_{col}} \times \sum_{(i,j) \in Col(\lambda)} Y_{i,j}(\lambda_{min} + p \times \Delta\lambda) \quad (6)$$

wherein $N_{col}$ is the number of pixels of the zone $Col(\lambda)$. The decision variable $X_{col}(\lambda)$ is then equal to $\gamma_{col}(\lambda_c)$. The unit 14 also calculates an error of measurement of the colony at the wavelength $\lambda_c$, in particular the standard deviation, denoted "SD", of all the values $\gamma_{i,j}(\lambda_c)$ of the pixels belonging to the pixel zone $Col(\lambda)$.

At 44, the unit 44 then applies the following comparison rules to the value of the spectrum $\gamma_{col}(\lambda_c)$:

if $\gamma_{col}(\lambda_c) < \gamma_{GN_{max}}(\lambda_c) + SD$ then the colony is Gram-negative (7)

if $\gamma_{col}(\lambda_c) > \gamma_{GP_{min}}(\lambda_c) - SD$ then the colony is Gram-positive (8)

if $\gamma_{col}(\lambda_c) \in [\gamma_{GP_{min}}(\lambda_c) - SD; \gamma_{GN_{max}}(\lambda_c) + SD]$ then the Gram is undetermined (9)

wherein $\gamma_{GN_{max}}(\lambda_c)$ and $\gamma_{GP_{min}}(\lambda_c)$ are two predefined thresholds, preferentially depending on the culture medium and stored in the unit 14. As a variant, the error of measurement SD can be chosen as zero.

FIG. 3A illustrates mean spectra $\gamma_{col}(\lambda)$ of colonies having grown on a transparent medium (in this case CPSE), namely 10 Gram-negative ("GN") strains (*Escherichia coli* (3 strains), *Enterobacter cloacae*, *Proteus mirabilis*, *Providencia stuartii*, *Serratia marcescens*, *K pneumoniae*, *Morganella morganii*, *Citrobacter freundii*) and 10 Gram-positive ("GP") strains (*Staphylococcus saprophyticus*, *Enterococcus faecalis* (2 strains), *Streptococcus agalactiae*, *Staphylococcus saprophyticus* (2 strains), *Streptococcus agalactiae*, *Enterococcus faecium*, *Streptococcus agalactiae*). FIG. 3B is a view in greater detail of the range 415 nm-440 nm. FIGS. 4A and 4B illustrate the same spectra, but for strains having grown on an opaque medium (in this case CPSO, different than CPSE in that it contains $SiO_2$ particles). As can be noted in these examples, at least in the range 415 nm-440 nm, the two Gram types differ from one another, the difference even being very marked for the opaque medium. In particular, in the range 415 nm-440 nm, it is observed that the spectra of the Gram-negative bacteria are below the spectra of the Gram-positive bacteria.

The first variant was tested on 30 bacterial strains, cultured for each culture medium, among the most commonly involved in clinical infections, namely (number of the strains per species between parentheses):

for Gram-negative: *Escherichia coli* (1), *K. pneumoniae* (1), *Klebsiella oxytoca* (1), *Proteus mirabilis* (1), *Morganella morganii* (1), *Stenotrophomonas maltophilia* (1), *Acinetobacter baumanii* (1), *Enterobacter cloacae* (1), *Serratia marcescens* (1), *Citrobacter koseri* (1), *Enterobacter aerogenes* (1), *Moraxella catarrhalis* (1), *Hafnia alvei* (1), *Pseudomonas aeruginosa* (1), *Haemophilus influenzae* (1);

for Gram-positive: *Corynebacterium jeikeium* (1), *Corynebacterium amycolatum* (1), *Enterococcus faecalis* (1), *Enterococcus faecium* (1), *Staphylococcus aureus* (1), *Staphylococcus epidermidis* (1), *Staphylococcus haemolyticus* (1), *Staphylococcus hominis* (1), *Streptococcus pneumoniae* (1), *Streptococcus agalactiae* (1), *Streptococcus pyogenes* (1), *Streptococcus anginosus* (1), *Streptococcus viridans* (1).

For each channel $\lambda$ of the range 415 nm-440 nm, the minimum $\gamma_{GP_{min}}(\lambda)$ of the spectra at the value $\lambda$ of the Gram-positive strains is determined. Likewise, the maximum $\gamma_{GN_{max}}(\lambda)$ of the spectra at the value $\lambda$ of the Gram-negative strains is determined. The channel $\lambda_c$ retained for the culture medium is then that which maximizes the range $[\gamma_{GP_{min}}(\lambda_c); \gamma_{GN_{max}}(\lambda_G)]$, and the predefined thresholds retained for the medium are, respectively, the values $\gamma_{GP_{min}}(\lambda_c)$ and $\gamma_{GN_{max}}(\lambda_c)$. For the CPSE medium, the Gram type of 19 strains of species identical to those listed above, including 10 Gram-positive strains and 9 Gram-positive strains, was predicted with a success rate close to 90%. For the CPSO medium, the success on these same strains is 100%.

In a second variant based on the first derivative of the reflectance, the unit 14 calculates, at 42, a spectrum of reflectance of the colony, e.g. a mean spectrum $\gamma_{col}(\lambda)$ on the pixels of the colony as described above, then calculates the first derivative $$\frac{\partial \gamma_{col}}{\partial \lambda}(\lambda)$$

or me mean spectrum. The decision variable $X_{col}(\lambda)$ is then equal to $$\frac{\partial \gamma_{col}}{\partial \lambda}(\lambda_c).$$

At 44, the unit 14 applies a prediction model to said variable, for example a linear model which discriminates according to the relationships:

$$Gram = b + a \times \frac{\partial \gamma_{col}}{\partial \lambda}(\lambda_c) \tag{10}$$

if Gram<0.5 then the colony is Gram-negative (11)

if Gram>0.5 then the colony is Gram-negative (12)

wherein Gram is a score, and the parameters a and b are predefined coefficients stored in the unit 14 and preferentially dependent on the culture medium.

The second variant was tested on 52 strains, 28 being Gram-negative and 24 being Gram-positive, belonging to 19 different species among the most commonly involved in clinical infections, namely (number of strains per species between parentheses):

for Gram-negative: *Escherichia coli* (9), *Klebsiella pneumoniae* (3), *Enterobacter cloacae* (1), *Serratia Marcescens* (2), *Citrobacter freundii* (2), *Proteus mirabilis* (2), *Providencia stuartii* (1), *Morganella morganii* (2);

for Gram-positive: *Staphylococcus saprophyticus* (9), *Streptococcus agalactiae* (7), *Enterococcus faecium* (3), *Enterococcus faecalis* (3), *Staphylococcus aureus* (1), *Candida albicans* (1).

Figure 6:
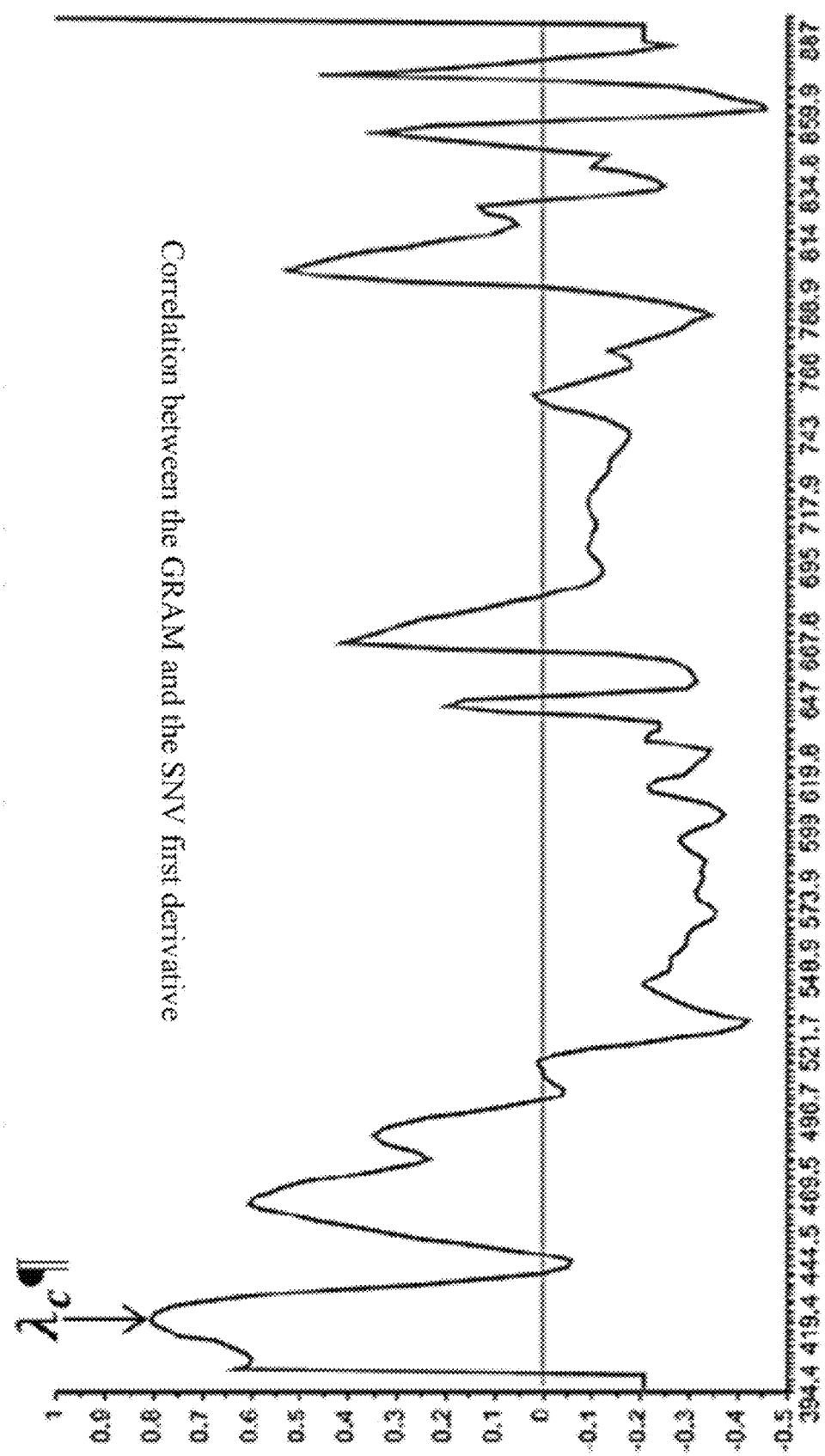
FIG. 6 is a plot illustrating the correlation obtained by a single-channel linear prediction model for the various acquisition wavelengths.
Figure 7:
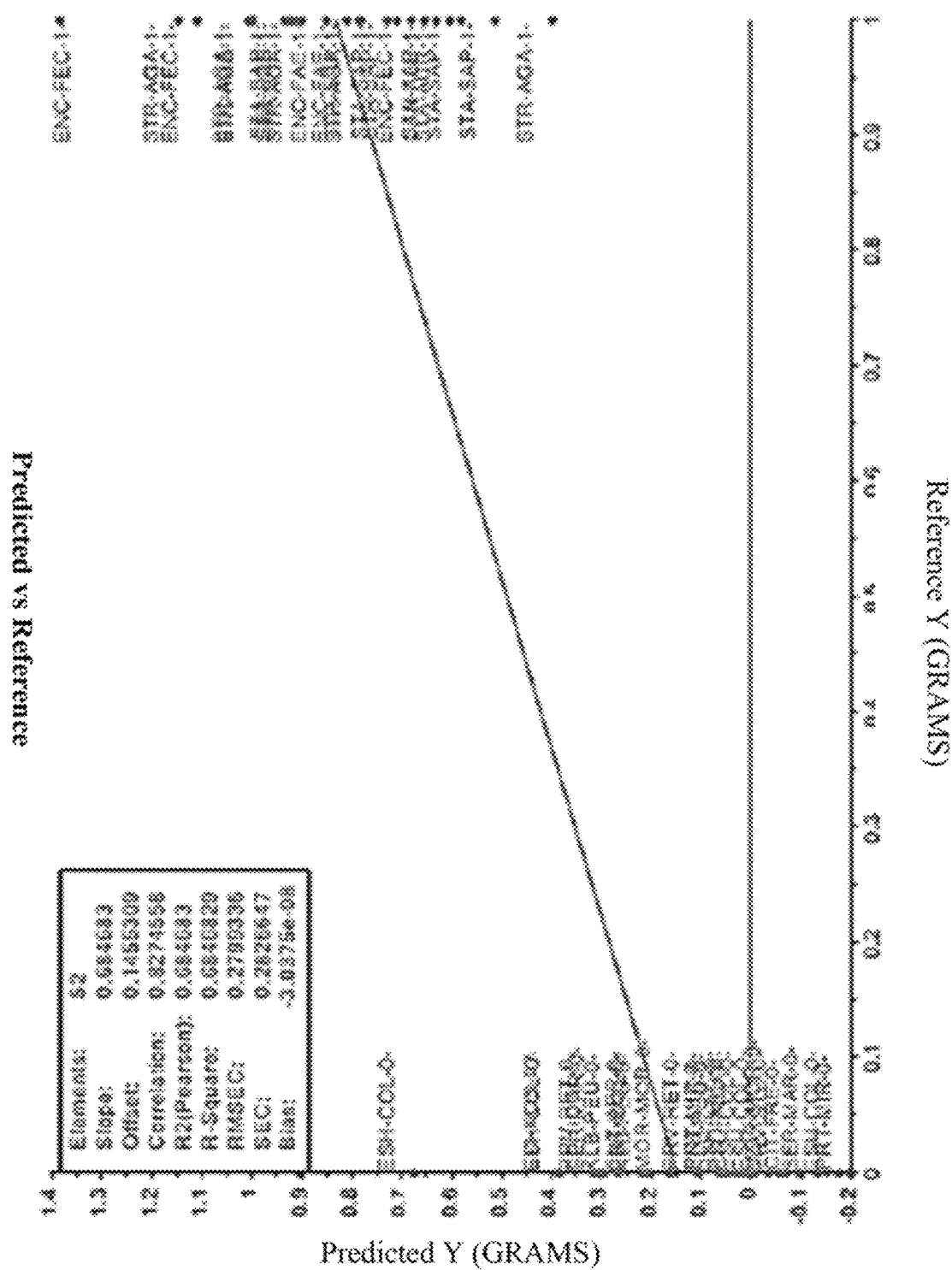
FIG. 7 is a plot illustrating results of prediction of the Gram type by means of the single-channel linear prediction model.

FIG. 5 illustrates the learning model for the relationship (10), the Gram-negative observed being assigned the value 0 and the Gram-positive observed being assigned the value 1. A linear regression between the observed and predicted Grams is carried out in order to determine the parameters a and b in a manner known per se. The model was learned for each wavelength of the range 400 nm-900 nm, and FIG. 6 illustrates the correlation coefficient as a function of the wavelength for a transparent culture medium (in this case CPSE). The maximum of this correlogram corresponds to the wavelength $\lambda_c$ and it is thus observed that the distinguishing character of the range 415 nm-440 nm is automatically found by linear regression, $\lambda_c$, in fact being equal to 415.3 nanometers. FIG. 7 illustrates the predicted Gram as a function of the known Gram of the strains described above for the CPSE medium, the success rate being greater than 80%. The success rate for an opaque medium is, moreover, 100%. Several decision variables were tested, the table of FIG. 8 listing said variables. It appears that the first and second derivatives of the non-normalized reflectance are the variables which lead to the highest success rate, the first derivative being, however, preferred according to the principle of parsimony.

B. Multi-Channel Approach

According to this approach, several channels of the wavelength range 415 nm-440 nm are used, advantageously and optionally in combination with channels of the range 750 nm-800 nm. The decision variable is $X_{col}(\lambda)$ is for example the mean spectrum reflectance (normalized or non-normalized), of absorbance (normalized or non-normalized), the first derivative or the second derivative over the whole of the range 400 nm-900 nm.

Figure 9:
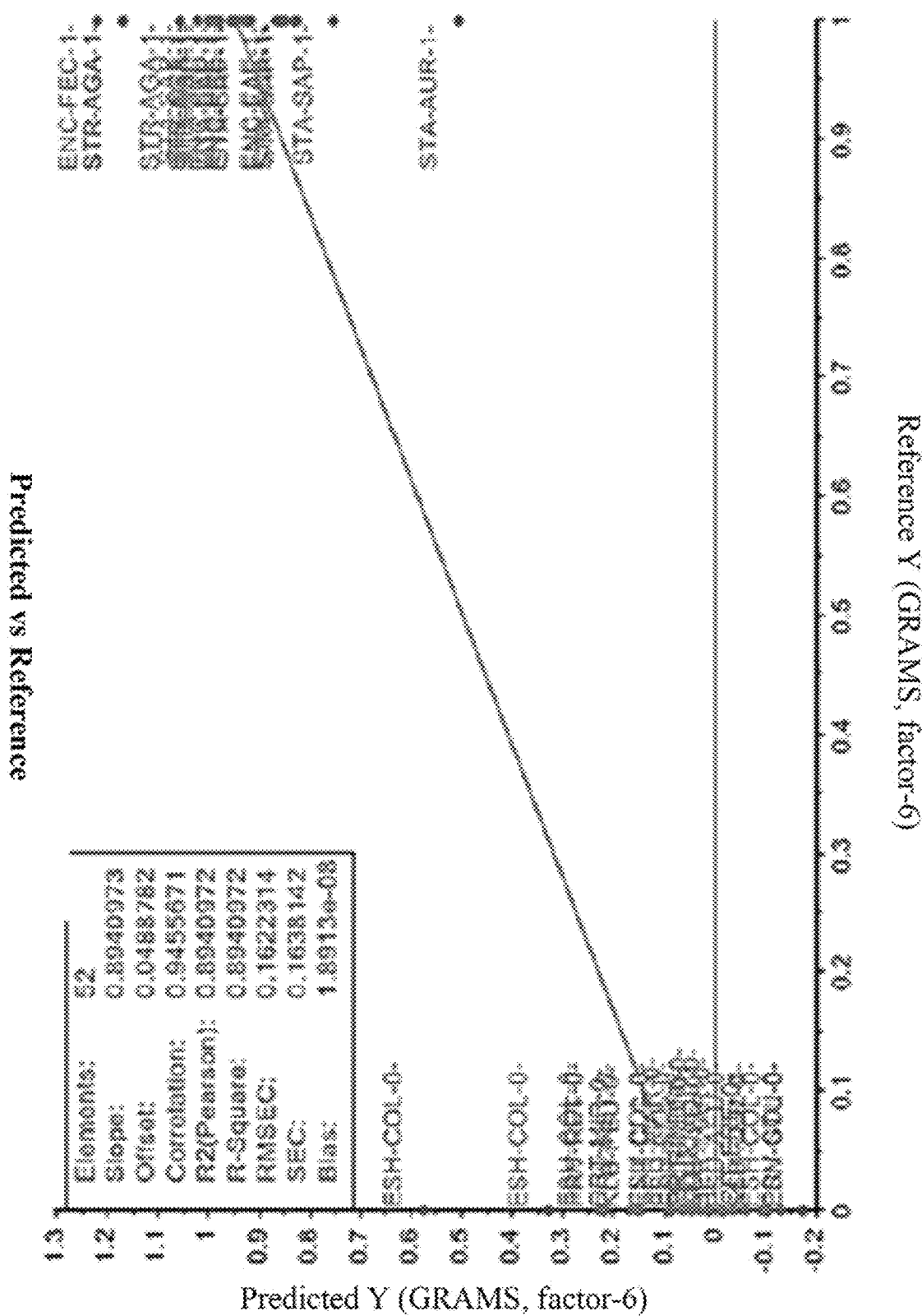
FIG. 9 is a plot illustrating results of prediction of the Gram type by means of a multi-channel linear prediction model.
Figure 10:
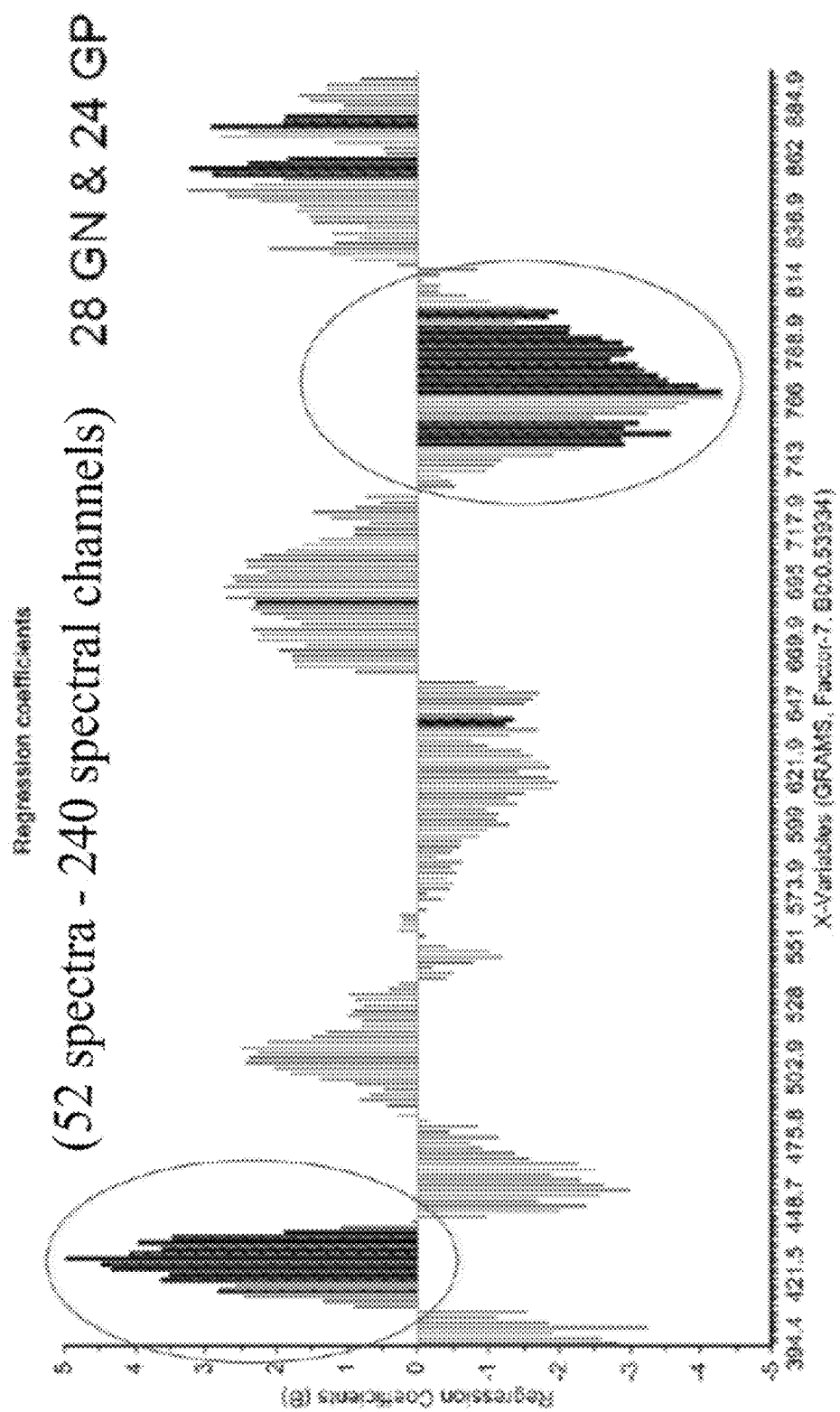
FIG. 10 is a plot illustrating the parameters of the multi-channel model as a function of the acquisition wavelengths.
Figure 11:
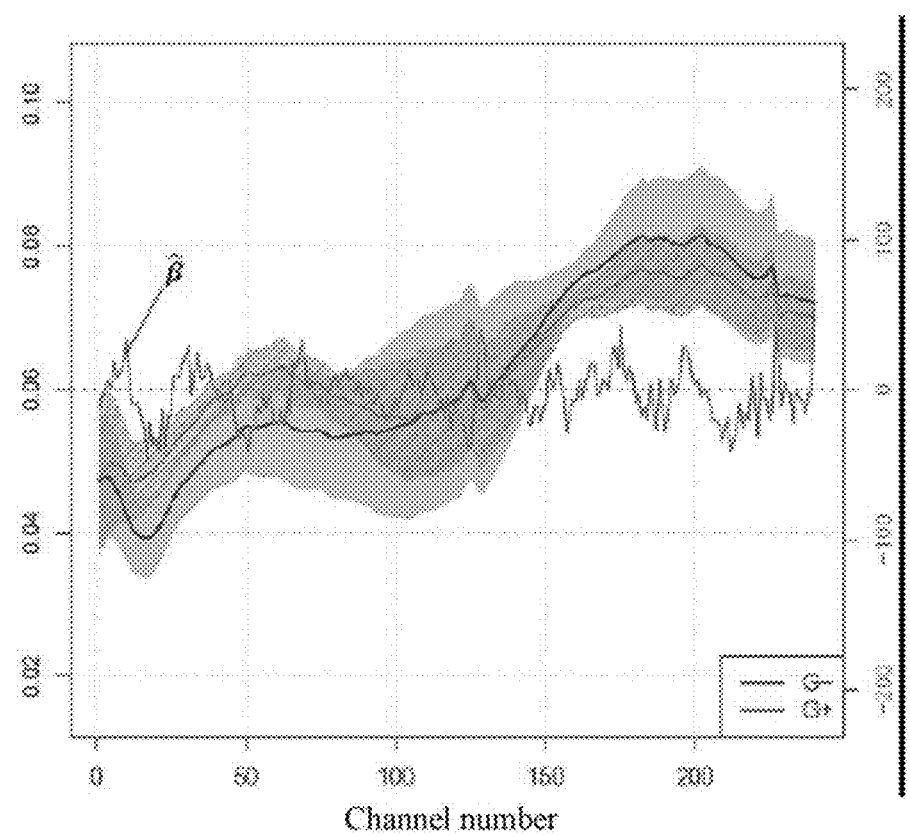
FIG. 11 is a plot illustrating the components of a prediction model based on an SVM classification as a function of the acquisition wavelengths.

According to a first variant, and for the reasons mentioned above, the first derivative of the non-normalized reflectance is used. The unit 14 thus calculates, at 42, the first derivative $$\frac{\partial \gamma_{col}(\lambda)}{\partial \lambda}$$

of the mean spectrum $\gamma_{col}(\lambda)$ over the range 400 nm-900 nm, as previously described, this derivative constituting the decision variable $X_{col}(\lambda)$. At 44, the unit 14 applies a prediction model to said variable, for example a linear model according to the relationships:

$$Gram = b + \sum_{p \in [0,P]} a_p \times \frac{\partial \gamma_{col}(\lambda_{min} + p \times \Delta\lambda)}{\partial \lambda} \tag{13}$$

if Gram<0.5 then the colony is Gram-negative (14)

if Gram>0.5 then the colony is Gram-positive (15)

wherein Gram is a score, and the parameters $a_p$ and b are predefined coefficients stored in the unit 14, and preferentially dependent on the culture medium. The prediction model for the relationship (13) is learned in a manner similar to that previously described, by linear regression. FIG. 9 illustrates the predicted Gram as a function of the observed Gram for the CPSE medium. For the latter, the degree of correlation is 95%. FIG. 10 illustrates the coefficients $a_p$. It is noted here that the prediction model uses two principal wavelength ranges in the prediction model, namely the range 415 nm-440 nm, and more particularly the range 421 nm-436 nm, and the range 750 nm-800 nm. It is thus observed that the range 750 nm-800 nm also comprises distinguishing spectral information concerning the Gram type of the bacteria.

According to a second variant, the decision variable is multi-channel and also multi-pixel, the spectral information of each pixel of the colony being used, and not averaged as previously described. As opposed to the term "mean", the spectral information associated with a pixel is denoted under the term "individual". In particular, the decision variable is $X_{col}(\lambda)$ consists of all of the individual spectra of reflectance (normalized or non-normalized), of absorbance (normalized or non-normalized), of their first derivatives or of their second derivatives, of the pixels of the zone $Col(\lambda)$.

For example, by considering the spectra of normalized reflectance $\{\gamma_{i,j}(\lambda)\}_{(i,j)\in Col(\lambda)}$ (e.g. by dividing each individual spectrum by its Euclidean norm) over the range 400 nm-900 nm, the unit 14 implements, at 44, a prediction rule based on a two-class classification (i.e. Gram-positive, assigned for example to the positive values, and Gram-negative, assigned for example to the negative values) according to the relationships:

$$\text{Gram} = X_{col}(\lambda) \cdot \hat{\beta} \quad (16)$$

$$\text{if } N\text{pos(Gram)} > N\text{neg(Gram), then the colony is Gram-positive} \quad (17)$$

$$\text{if } N\text{pos(Gram)} < N\text{neg(Gram), then the colony is Gram-negative} \quad (18)$$

where Gram is a dimension vector equal to the number P of channels in the range 400 nm-900 nm, $X_{col}(\lambda)$ is in this case a matrix of which the rows are respectively equal to the normalized individual spectra of reflectance $\{\gamma_{i,j}(\lambda)\}_{(i,j)\in Col(\lambda)}$, $\hat{\beta}$ is a predefined column vector of dimension equal to P, Npos(Gram) is the number of components of the Gram vector which are positive and Nneg(Gram) is the number of components of the Gram vector which are negative. The parameters $\hat{\beta}$ and $\beta_0$, stored in the unit 14, are preferentially dependent on the culture medium. The prediction, based on a majority vote, can as a variant be made on the mean of the vector $\hat{\beta}$, Gram-negative being predicted if this mean is negative and Gram-positive being predicted if this mean is positive.

In a first example, the prediction model for the relationship (14) is learnt on the basis of the pixels of the 52 strains previously described by resolving a problem of optimization of SVM (for Support Vector Machine) type according to the following relationships:

$$\beta = \arg\min_{\beta, \xi_m} \left( \frac{1}{2} \|\beta\|^2 + C \sum_{m=1}^{M} \xi_m \right) \quad (19)$$

under the constraints:

$$\forall m \in [1, M]: \xi_m \geq 0 \quad (21)$$

$$\forall m \in [1, M]: q_m(\Upsilon_m(\lambda) \cdot \beta) \geq 1 - \xi_m \quad (22)$$

$$\|\beta\|^2 + C \sum_{m=1}^{M} \xi_m$$

wherein N is the number of normalized individual spectra of reflectance, denoted $\gamma_m(\lambda)$, used for the learning, numbered from 1 to M, $q_m \in \{-1, 1\}$ with $q_m = 1$ if the $m^{th}$ spectrum is associated with a Gram-positive bacterium, and $q_m = -1$ if the $m^{th}$ spectrum is associated with a Gram-negative bacterium, and C is a predefined scalar.

The model was validated on 10 Gram-negative strains (*Escherichia coli* (3 strains), *Enterobacter cloacae*, *Proteus mirabilis*, *Providencia stuartii*, *Serratia marcescens*, *K pneumoniae*, *Morganella morganii*, *Citrobacter freundii*) and 10 Gram-positive strains (*Staphylococcus saprophyticus*, *Enterococcus faecalis* (2 strains), *Streptococcus agalactiae*, *Staphylococcus saprophyticus* (2 strains), *Streptococcus agalactiae*, *Enterococcus faecium*, *Streptococcus agalactiae*). For an opaque medium (e.g. CPSO), the success rate is 100%. For a transparent medium (e.g. CPSE), the success rate is close to 94% for the Gram-negative bacteria and close to 98% for the Gram-positive bacteria. As can be noted in FIG. 10, which shows the components of the vector $\hat{\beta}$ as a function of the channels, the prediction based on the SVM classification does not allow the emergence of a particular range of wavelengths.

Figure 12:
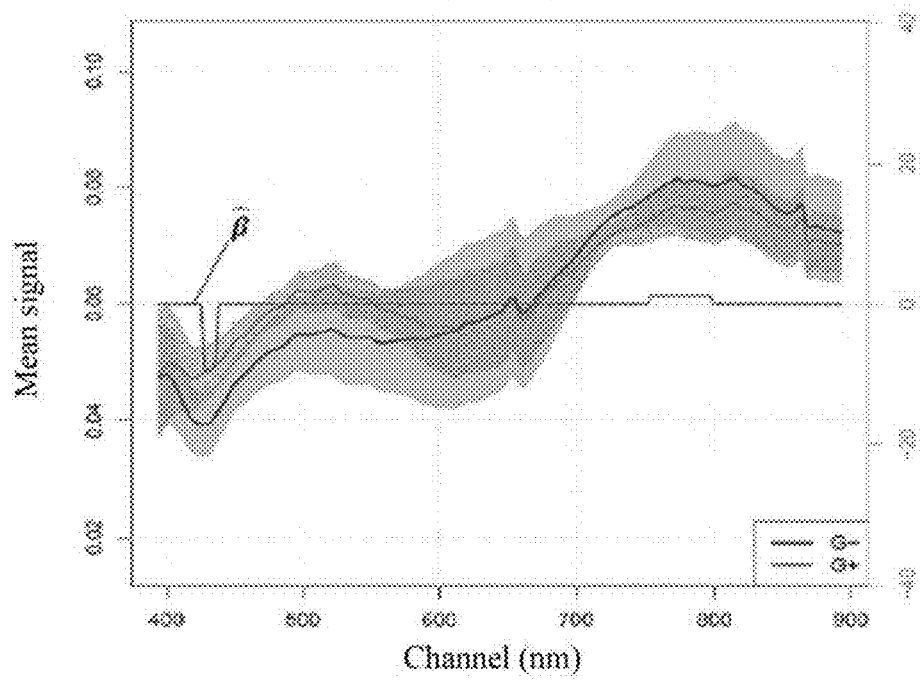
FIG. 12 is a plot illustrating the components of a prediction model based on learning of "fused Lasso" type as a function of the acquisition wavelengths.

In a second example, the prediction model for the relationship (14), with has been learnt on the basis of the pixels of the 52 strains previously described by resolving a problem of optimization of "Fused Lasso" type according to the following relationship:

$$\hat{\beta} = \arg\min_{\beta} \left( \|q_m - \Upsilon_m(\lambda)\|_2^2 + \mu_1 \sum_{p=1}^{P} |\beta_p| + \mu_2 \sum_{p=1}^{P-1} |\beta_{p+1} - \beta_p| \right) \quad (23)$$

wherein $\mu_1$ and $\mu_2$ are two parameters which regulate, respectively, the parsimony of the model (i.e. the number of components of $\hat{\beta}$ which are not zero) and the regularity of the model (i.e. the variability between two successive components of $\hat{\beta}$). As can be seen in FIG. 12, when the parsimony and the regularity are forced during the learning of $\hat{\beta}$ ($\mu_1 = 0.0001$ and $\mu_2 = 0.0025$), the non-zero components of $\hat{\beta}$ automatically retained are those of the ranges 415 nm-440 nm and 750 nm-800 nm. The success rate is 100% for an opaque medium (e.g. CPSO), and for a transparent medium (e.g. CPSE), the success rate is 92% for Gram-positive and 84% for Gram-negative.

An acquisition by means of a hyperspectral camera in the range 400 nm-900 nm has been described. Obviously, the invention also applies to an acquisition carried out by a multispectral camera which acquires spectra in two separate ranges comprising, or consisting of, respectively, the ranges 415 nm-440 nm and 750 nm-800 nm. Likewise, the invention applies two distinct cameras configured for respectively acquiring these ranges.

An acquisition in a broader range than the range 415 nm-440 nm has been described, in particular an acquisition in the range 750 nm-800 nm which comprises spectral information distinguishing the Gram type of the bacteria. As a variant, the acquisition is carried out only in the range 400 nm-500 nm, more preferentially in the range 415 nm-440 nm, and the prediction of the Gram type is carried out only as a function of the spectral information from this range. Obviously, the invention applies to any acquisition range comprising the range 415 nm-440 nm, combined with processing carried out only over this range for predicting the Gram type.

Image acquisition, that is to say the acquisition of spatial and spectral information, has been described. Quite obviously, the invention also applies to the acquisition of solely spectral information, for example by means of microspectroscopy. For example, a colony may be localized beforehand by means of a standard imaging system or by an operator, and then a reflection or transmission spectrum emitted by the colony is acquired by microspectroscopy and processed in order to predict the Gram type.

Figure 13A:
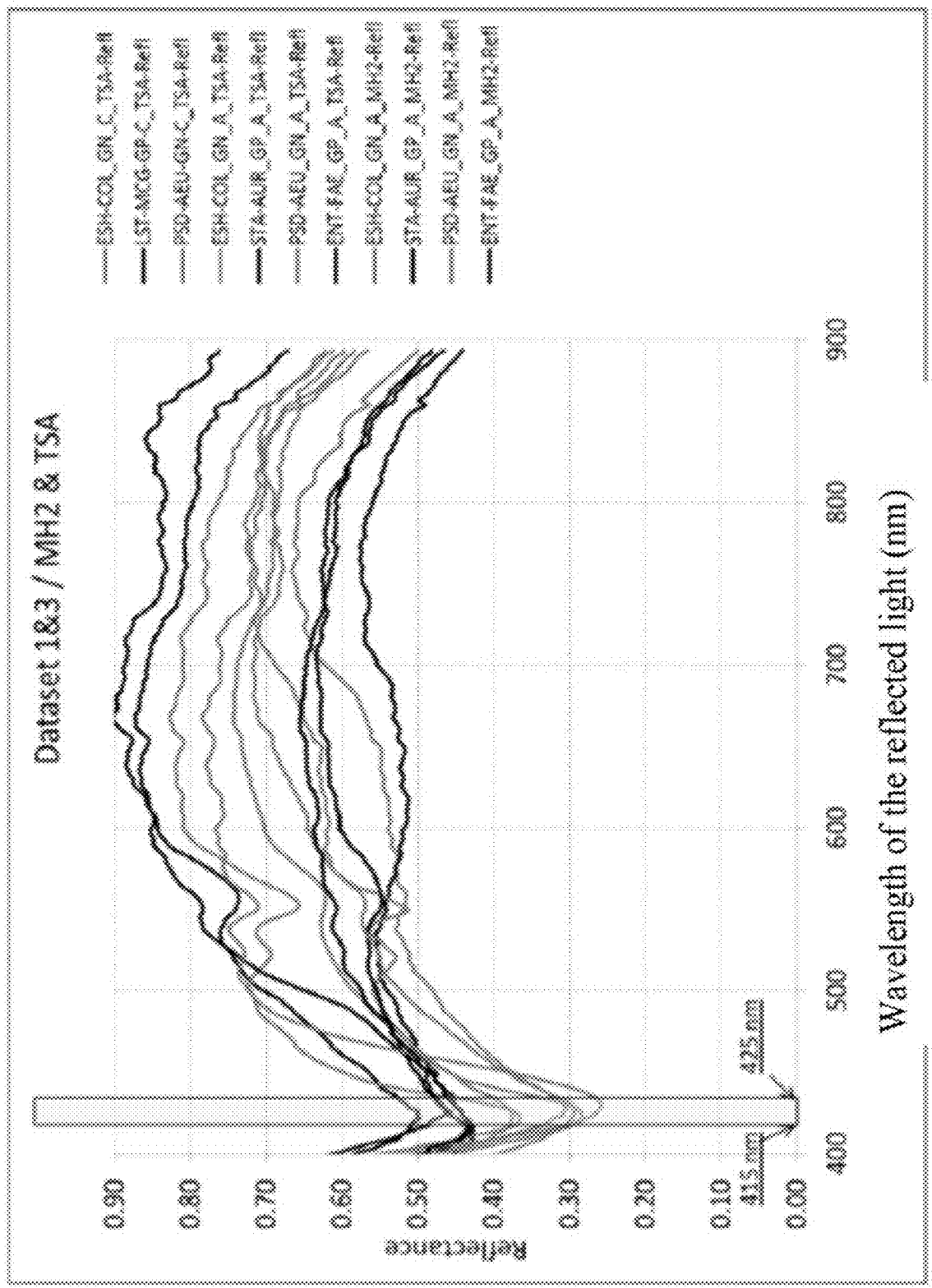
FIGS. 13A and 13B are plots illustrating spectra of reflectance of bacterial colonies having grown on a TSA and an MH2 medium.
Figure 13B:
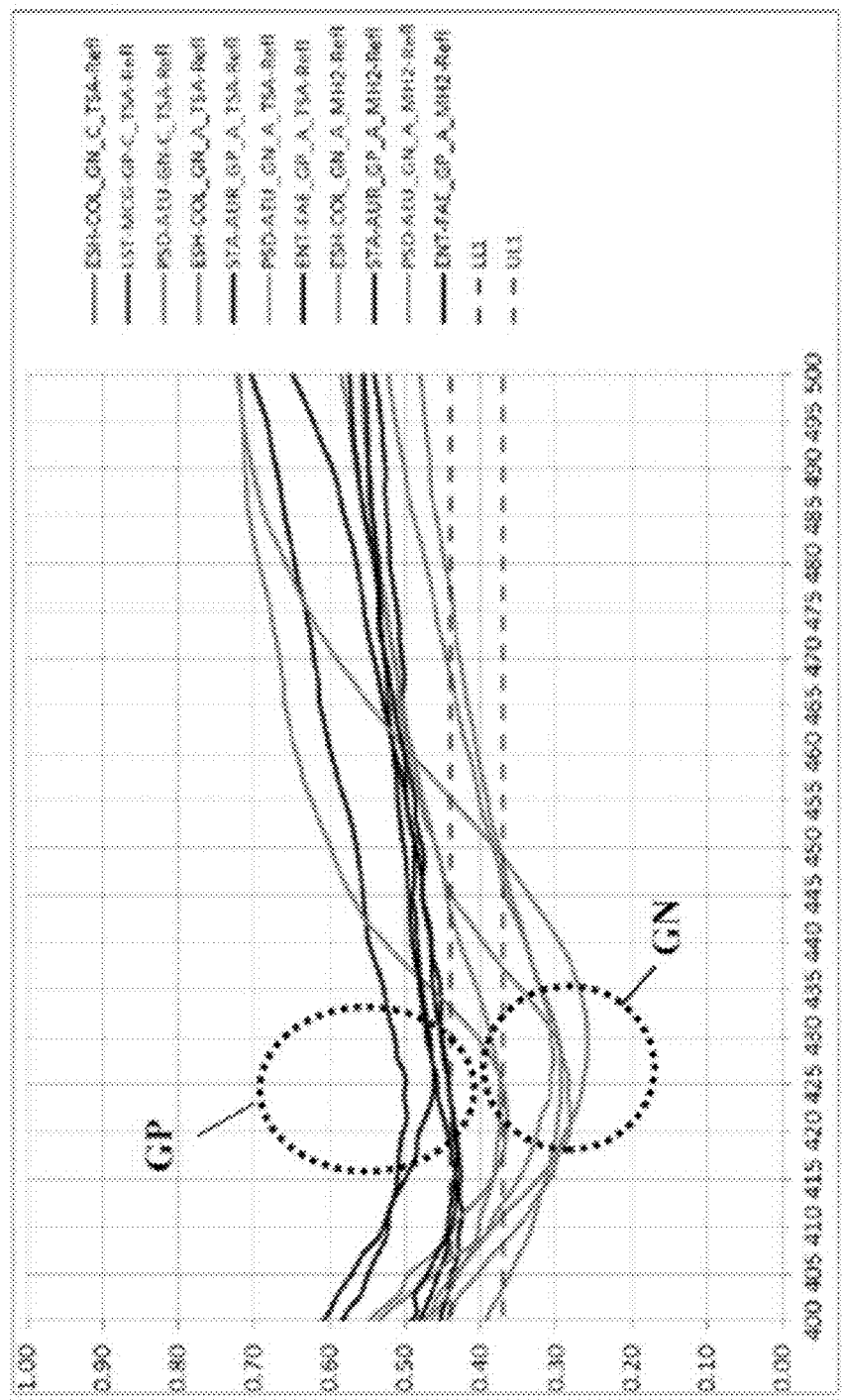

Two culture media, CPSE (transparent) and CPSO (opaque) have been described. Other culture media were tested, giving analogous results. For example, in FIGS. 13A and 13B, it is observed, on TSA (tryptone casein soy agar) and MH2 (Mueller Hinton 2 agar) culture media, that Gram-positive and Gram-negative differ from one another at least over the range 415 nm-440 nm. As previously described, the opaque media are preferred since they facilitate the prediction of the Gram type. The invention thus applies to any type of transparent and non-colored culture medium, e.g. those of the prior art, to which an opacifier, for example $SiO_2$ particles, is added.

Various predictions have been described (thresholding, linear model, SVM, Lasso). Of course, the invention applies to any type of processing which makes it possible to classify measurements in two classes (Gram-positive and Gram-negative), for example a spectrum comparison algorithm (e.g. a centroid method), a neuronal network-based classification, a tree-based classification (e.g. CART, for "classification and regresssion tree", algorithm), etc. Such methods are, for example, those described in the document by Eric Laloum, "*Une méthode chimiométrique originate d'identification de produits par spectroscopic proche infrarouge*" ["An original chemometric method for identifying products by near infrared spectroscopy"], Spectra Analyse, vol. 33, No. 237, 2004.

Embodiments based on a reflection spectrum have been described. As a variant, the spectrum is acquired in transmission, with the processing operations previously described for the prediction of the Gram type applying.

The invention claimed is:

1. A process of imaging of a bacterial strain in a sample, comprising:
    illuminating at least one colony of the bacterial strain grown on an opaque nutritive medium with a light in a wavelength range of 415 nm-440 nm, to which the bacterial strain has a natural electromagnetic response; and
    measuring the intensity of the light that is reflected by, or transmitted through, the colony illuminated by the light.

2. The process as claimed in claim 1, further comprising:
    illuminating the colony with a second light in a wavelength range of 750 nm-800 nm, to which the bacterial strain has a natural electromagnetic response; and
    measuring the intensity of the second light that is reflected by, or transmitted through, the colony illuminated by the second light.

3. The process as claimed in claim 1, wherein the measured light that is reflected by, or transmitted through, the colony is in a wavelength of 420 nm.

4. The process as claimed in claim 1, wherein the opaque nutritive medium has a reflectance $\rho$ of less than or equal to 10%.

5. The process as claimed in claim 1, wherein the opaque nutritive medium has a reflectance $\rho$ of less than or equal to 5%.

6. The process as claimed in claim 1, further comprising:
    acquiring a hyperspectral or multispectral image of the colony; and
    determining the light intensity as the mean of at least one pixel of the image.

* * * * *